United States Patent [19]

Pitteloud et al.

[11] Patent Number: 5,098,945
[45] Date of Patent: Mar. 24, 1992

[54] 2,4-DIMETHYL-6-S-ALKYLPHENOLS

[75] Inventors: Rita Pitteloud, Praroman; Paul Dubs, Marly, both of Switzerland

[73] Assignee: Ciba-Geigy Corporation, Ardsley, N.Y.

[21] Appl. No.: 654,415

[22] Filed: Feb. 11, 1991

Related U.S. Application Data

[63] Continuation of Ser. No. 542,238, Jun. 22, 1990, abandoned.

[30] Foreign Application Priority Data

Jun. 30, 1989 [CH] Switzerland ..................... 2435/89

[51] Int. Cl.$^5$ ..................... C07C 39/06; C08K 5/13
[52] U.S. Cl. ..................... 524/349; 524/304; 524/350; 568/780; 568/786; 568/788; 568/794
[58] Field of Search ..................... 524/304, 349, 350; 568/780, 786, 788, 794

[56] References Cited

U.S. PATENT DOCUMENTS

| | | | |
|---|---|---|---|
| 2,073,995 | 3/1937 | Raiziss et al. | 568/780 |
| 2,198,349 | 4/1940 | Read | 568/780 |
| 2,202,877 | 6/1940 | Stevens et al. | 568/788 |
| 2,205,947 | 6/1940 | Flett | 568/794 |
| 2,605,251 | 7/1952 | Kitchen et al. | 568/780 |
| 3,082,258 | 3/1963 | McConnell et al. | 568/768 |
| 3,290,389 | 12/1966 | Hahn | 260/619 |
| 3,347,938 | 10/1967 | Bell et al. | 568/780 |
| 3,367,981 | 2/1968 | Napalitana | 260/624 |
| 3,394,020 | 7/1968 | Bell et al. | 106/270 |
| 3,511,802 | 5/1970 | Newland et al. | 524/351 |
| 3,929,912 | 12/1975 | Hervert | 260/624 |
| 4,405,818 | 9/1983 | Stead et al. | 568/781 |
| 4,954,663 | 9/1990 | Marler et al. | 568/794 |

FOREIGN PATENT DOCUMENTS

| | | |
|---|---|---|
| 291915 | 11/1988 | European Pat. Off. |
| 1142873 | 8/1963 | Fed. Rep. of Germany |
| 1182020 | 9/1985 | U.S.S.R. ..................... 568/794 |
| 1491995 | 11/1977 | United Kingdom |

OTHER PUBLICATIONS

CA 72:11860t (1970).
CA:69:10147s (1968).
CA 99:40872m (1983).
Kenneth A. Gould et al: Ind. Eng. Chem. Fundam. 1983, 22(3) 308-11 (Eng.)
Gerald Scott: Atmospheric Oxidation & Antioxidants (1965), pp. 120-125, 225-230, 330-361.
Kurasher et al. Synthesis and Crystal Structure of 2,4,6-Tri(d,d-dimethylbenzyl)Phenyl pp. 1673-1676 (1957).
Loran et al. Chemistry and Industry pp. 34-35 (1/5/87)
Konlikovski et al. pp. 1702-1707 (1988).
Chemical Abstract No. 210202e (1986).

*Primary Examiner*—Veronica P. Hoke
*Attorney, Agent, or Firm*—JoAnn Villamizar

[57] ABSTRACT

A composition containing a) a polystyrene, substituted polystyrene, copolymer or terpolymer of styrene or of a substituted styrene, polycarbonate, polyester-carbonate, polyurethane, polyamide copolyamide, polyacetyl or polyphenylene oxide and b) at least one compound of the formula I

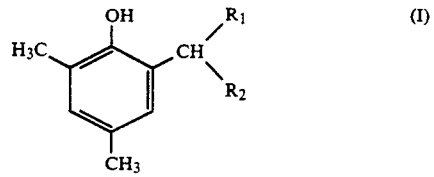

in which $R_1$ is methyl or ethyl and $R_2$ is $C_2$-$C_{30}$ alkyl.

Compounds of the formula I in which $R_2$ is $C_8$-$C_{30}$alkyl are novel and are suitable for stabilizing organic materials against thermal, oxidative and actinic degradation.

14 Claims, No Drawings

2,4-DIMETHYL-6-S-ALKYLPHENOLS

This application is a continuation of application Ser. No. 542,238, filed June 22, 1990 now abandoned.

The present invention relates to compositions containing selected organic polymers, for example an acrylonitrile/butadiene/styrene terpolymer, and 2,4-dimethyl-6-s-alkylphenols, and to novel 2,4-dimethyl-6-s-alkylphenols and to organic material stabilized therewith against thermal, oxidative and actinic degradation.

A number of trialkylphenols, for example 2,6-di-tert-butyl-4-methylphenol (®Swanox BHT) and their use for stabilizing organic material are known. In "Atmospheric Oxidation and Antioxidants; Elsevier Publishing Company (1965), pages 120–125", G. Scott describes the connection between stabilizing action and substitution in the phenol, for mineral oils. The stabilization of polypropylene resins by means of alkyl-substituted phenols is disclosed in U.S. Pat. No. 3,511,802. The preparation and the spectra of secondary alkylphenols are mentioned in Chemical Abstracts 69:10,147s and 72:11,860t.

The present invention relates to compositions containing a) a polystyrene, substituted polystyrene, copolymer or terpolymer of styrene or of a substituted styrene, polycarbonate, polyester-carbonate, polyurethane, polyamide, copolyamide, polyacetal or polyphenylene oxide and b) at least one compound of the formula I

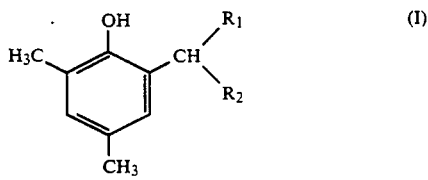

in which $R_1$ is methyl or ethyl and $R_2$ is $C_2$–$C_{30}$alkyl.

$R_2$ is, for example, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, heneicosyl, docosyl, tricosyl, tetracosyl, pentacosyl, hexacosyl, heptacosyl, octacosyl, nonacosyl or triacontyl.

$R_2$ is preferably $C_8$–$C_{30}$alkyl, for example $C_8$–$C_{18}$alkyl or $C_{10}$–$C_{30}$alkyl. It is particularly preferable for $R_2$ to be $C_{12}$–$C_{18}$alkyl.

Compositions of interest are those in which the compound of the formula I is

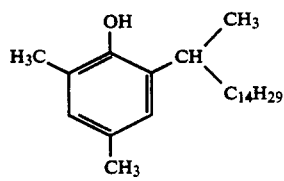

or

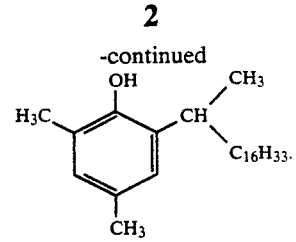

Compositions which are also of interest are those containing a mixture of the compounds

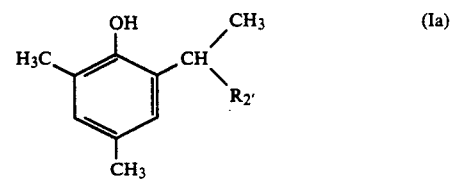

and

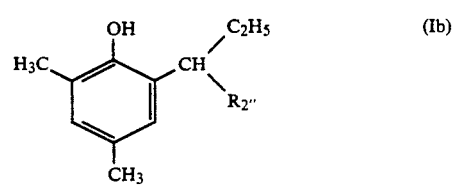

in which $R_2'$ is $-C_mH_{2m+1}$ and $R_2''$ is $-C_{m-1}H_{2m-1}$ and m is an integer from 2 to 30 and is the same in the radicals $R_2'$ and $R_2''$.

The ratio by weight of the compounds (Ia)/(Ib) is, for example, 1/99 to 99/1, preferably 99/1 to 70/30 and particularly 95/5 to 80/20.

Compositions which are preferred are also those wherein the component a) is a polystyrene, substituted polystyrene or a copolymer or terpolymer of polystyrene or of a substituted polystyrene. The following may be mentioned as examples:

1) Polystyrene, poly-(p-methylstyrene) or poly-(α-methylstyrene).

2) Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/maleic anhydride or styrene/acrylonitrile/methyl acrylate; mixtures of high impact strength formed from styrene copolymers and another polymer, for example a polyacrylate, a diene polymer or an ethylene/propylene/diene terpolymer; and also block copolymers of styrene, for example styrene/butadiene/styrene, styrene/isoprene/styrene, styrene/ethylene-butylene/styrene or styrene/ethylene-propylene/styrene.

3) Graft copolymers of styrene or α-methylstyrene, for example styrene on polybutadiene, styrene on polybutadiene/styrene or polybutadiene/acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene, styrene and alkyl acrylates or alkyl methacrylates on polybutadiene, styrene and acrylonitrile on ethylene/propylene/diene terpolymers, styrene and acrylonitrile on polyalkyl acrylates or polyalkyl methacrylates, styrene and acrylonitrile on acrylate/butadiene copolymers and mixtures thereof with the copolymers mentioned under 2), such as are known, for example, as so-called ABS, MBS, ASA or AES polymers.

Components a) which are particularly preferred are impact-resistant polystyrene (IPS), styrene/acrylonitrile copolymers (SAN) and acrylonitrile/butadiene/styrene terpolymers (ABS), in particular acrylonitrile/butadiene/styrene terpolymers (ABS) and methyl methacrylate/butadiene/styrene graft copolymers (MBS).

Components a) which are of interest are also polycarbonate, polyester-carbonate, polyurethane, polyamide, copolyamide, polyacetal and polyphenylene oxide. The following may be mentioned as examples:

I) Polyurethanes derived on the one hand from polyethers, polyesters and polybutadienes having terminal hydroxyl groups and, on the other hand, from aliphatic or aromatic polyisocyanates, and precursors thereof.

II) Polyamides and copolyamides derived from diamines and dicarboxylic acids and/or from aminocarboxylic acids or the corresponding lactams, such as polyamide 4, polyamide 6, polyamide 6/6, 6/10, 6/9, 6/12 or 4/6, polyamide 11, polyamide 12, aromatic polyamides originating from m-xylene, diamine and adipic acid; polyamides prepared from hexamethylenediamine and isophthalic and/or terephthalic acid and, if appropriate, an elastomer as modifier, for example poly-2,4,4-trimethylhexamethyleneterephthalamide or poly-m-phenyleneisophthalamide. Block copolymers of the polyamides mentioned above with polyolefins, olefin copolymers, ionomers or chemically linked or grafted elastomers; or with polyethers, for example with polyethylene glycol, polypropylene glycol or polytetramethylene glycol. Also polyamides or copolyamides modified with EPDM or ABS; and polyamides which have been condensed during processing ("RIM polyamide systems").

III) Polyacetals, such as polyoxymethylene, and polyoxymethylenes containing comonomers, for example ethylene oxide; polyacetals which have been modified with thermoplastic polyurethanes, acrylates or MBS.

The compounds of the formula I in which $R_1$ is methyl or ethyl and $R_2$ is $C_8$–$C_{30}$alkyl are novel and constitute a further subject of the invention.

Preferred meanings of $R_2$ can be deduced from the preceding statements.

The invention also relates to compositions containing an organic material which is sensitive to oxidative, thermal or actinic degradation and at least one compound of the formula I in which $R_1$ is methyl or ethyl and $R_2$ is $C_8$–$C_{30}$alkyl.

Examples of organic materials are those indicated above under 1)-3) and I)-III) and also 1. Polymers of monoolefins and diolefins, for example polypropylene, polyisobutylene, polybut-1-ene, polymethylpent-1-ene, polyisoprene or polybutadiene, and also polymers of cycloolefins, for example cyclopentene or norbornene; and also polyethylene (which can, if appropriate, be crosslinked), for example high-density polyethylene (HDPE), low-density polyethylene (LDPE) and linear, low-density polyethylene (LLDPE), 2. Mixtures of the polymers mentioned under 1), for example mixtures of polypropylene with polyisobutylene, polypropylene with polyethylene (for example PP/HDPE or PP/LDPE) and mixtures of different types of polyethylene (for example LDPE/HDPE), 3. Copolymers of monoolefins and diolefins with one another or with other vinyl monomers, for example ethylene/propylene copolymers, linear, low-density polyethylene (LLDPE) and mixtures thereof with low-density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers or ethylene/acrylic acid copolymers and salts thereof (ionomers), and also terpolymers of ethylene with propylene and a diene, such as hexadiene, dicyclopentadiene or ethylidenenorbornene; and also mixtures of such copolymers with one another and with polymers mentioned under 1), for example polypropylene-ethylene/propylene copolymers, LDPE-ethylene/vinyl acetate copolymers, LDPE-ethylene/acrylic acid copolymers, LLDPE-ethylene/vinyl acetate copolymers and LLDPE-ethylene/acrylic acid copolymers, 3a. Hydrocarbon resins (for example $C_5$–$C_9$), including hydrogenated modifications thereof (for example tackifier resins), 4. Polymers containing halogen, for example polychloroprene, chlorinated rubber, chlorinated or chlorosulfonated polyethylene, epichlorohydrin homopolymers and copolymers, especially polymers formed from vinyl compounds containing halogen, for example polyvinyl chloride, polyvinylidene chloride, polyvinyl fluoride or polyvinylidene fluoride; and copolymers thereof, such as vinyl chloride/vinylidene chloride, vinyl chloride/vinyl acetate or vinylidene chloride/vinyl acetate.

5. Polymers derived from $\alpha,\beta$-unsaturated acids and derivatives thereof, such as polyacrylates and polymethacrylates, polyacrylamides and polyacrylonitriles, 6. Copolymers of the monomers mentioned under 5) with one another or with other unsaturated monomers, for example acrylonitrile/butadiene copolymers, acrylonitrile/alkyl acrylate copolymers, acrylonitrile/alkoxyalkyl acrylate copolymers, acrylonitrile/vinyl halide copolymers or acrylonitrile/alkyl methacrylate/butadiene terpolymers, 7. Polymers derived from unsaturated alcohols and amines and acyl derivatives or acetals thereof, such as polyvinyl alcohol, polyvinyl acetate, stearate, benzoate or maleate, polyvinylbutyral, polyallyl phthalate or polyallylmelamine; and copolymers thereof with olefins mentioned in item 1, 8. Homopolymers and copolymers of cyclic ethers, such as polyalkylene glycols, polyethylene oxide, polypropylene oxide or copolymers thereof with bisglycidyl ethers, 9. Polyphenylene sulfides and mixtures thereof with styrene polymers or polyamides, 10. Polyureas, polyimides, polyamide-imides and polybenzimidazoles, 11. Polyesters derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate and polyhydroxybenzoates, and also block polyetheresters derived from polyethers having terminal hydroxyl groups; and also polyesters modified with polycarbonates or MBS,
12. Polysulfones, polyether-sulfones and polyetherketones,
13. Crosslinked polymers derived on the one hand from aldehydes and, on the other hand, from phenols, urea or melamine, such as phenol-formaldehyde, urea-formaldehyde and melamine-formaldehyde resins,
14. Drying and non-drying alkyd resins,
15. Unsaturated polyester resins derived from copolyesters of saturated and unsaturated dicarboxylic acids with polyhydric alcohols and also vinyl compounds as crosslinking agents, and also halogen-containing modifications thereof of low flammability,
16. Crosslinkable acrylic resins derived from substituted acrylic acid esters, for example from epoxyacrylates, urethane-acrylates or polyester-acrylates,
17. Alkyd resins, polyester resins and acrylate resins which are crosslinked with melamine resins, urea resins, polyisocyanates or epoxy resins,
18. Crosslinked epoxy resins derived from polyepoxides, for example from bisglycidyl ethers or from cycloaliphatic diepoxides;
19. Natural polymers, such as cellulose, natural rubber, gelatine and polymer-homologously chemically modified derivatives thereof, such as cellulose acetates, propionates and butyrates, and the cellulose ethers, such as methylcellulose; and also colophony resins and derivatives,
20. Mixtures (polyblends) of the abovementioned polymers, for example PP/EPDM, polyamide-/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP and PA/PPO,
21. Natural and synthetic organic materials which are pure monomeric compounds or mixtures thereof, for example mineral oils, animal or vegetable fats, oils and waxes, or oils, waxes and fats based on synthetic esters (for example phthalates, adipates, phosphates or trimellitates) and mixtures of synthetic esters with mineral oils in any desired ratios by weight, such as are used, for example, as spin finishes, and aqueous emulsions thereof and
22. Aqueous emulsions of natural or synthetic rubbers, for example natural rubber latex or latices of carboxylated styrene/butadiene copolymers.

The compositions according to the invention appropriately contain 0.01 to 10%, preferably 0.05 to 5% and particularly 0.1 to 2% of at least one compound of the formula I, relative to the total weight of the organic material to be stabilized.

In addition to a compound of the formula I, the compositions according to the invention can contain, in addition, conventional additives, for example:

1. Antioxidants 1.1. Alkylated monophenols, for example 2,6-di-tert-butyl-4-methylphenol,
2-tert-butyl-4,6-dimethylphenol, 2,6-di-tert-butyl-4-ethylphenol,
2,6-di-tert-butyl-4-n-butylphenol, 2,6-di-tert-butyl-4-isobutylphenol,
2,6-di-cyclopentyl-4-methylphenol, 2-(α-methylcyclohexyl)-4,6-dimethylphenol,
2,6-di-octadecyl-4-methylphenol, 2,4,6-tricyclohexylphenol,
2,6-di-tert-butyl-4-methoxymethylphenol and 2,6-dinonyl-4-methylphenol.

1.2. Alkylated hydroquinones, for example 2,6-di-tert-butyl-4-methoxyphenol,
2,5-di-tert-butylhydroquinone, 2,5-di-tert-amylhydroquinone and
2,6-diphenyl-4-octadecyloxyphenol.

1.3. Hydroxylated thiodiphenyl ethers, for example 2,2'-thiobis-(6-tert-butyl-4-methylphenol), 2,2'-thiobis-(4-octylphenol), 4,4' thiobis-(6-tert-butyl-3-methylphenol) and 4,4'-thiobis-(6-tert-butyl-2-methylphenol).

1.4. Alkylidene bisphenols, for example 2,2'-methylene-bis-(6-tert-butyl-4-methylphenol),
2,2'-methylenebis-(6-tert-butyl-4-ethylphenol),
2,2'-methylenebis-[4-methyl-6-(α-methylcyclohexyl)-phenol],
2,2'-methylenebis-(4-methyl-6-cyclohexylphenol),
2,2'-methylenebis-(6-nonyl-4-methylphenol), 2,2'-methylenebis-(4,6-di-tert-butylphenol),
2,2'-ethylidenebis-(4,6-di-tert-butylphenol),
2,2'-ethylidenebis-(6-tert-butyl-4-isobutylphenol),
2,2'methylenebis-[6-(α-methylbenzyl)-4-nonylphenol],
2,2'-methylenebis-[6-(α,α-dimethylbenzyl)-4-nonylphenol],
4,4'-methylenebis-(2,6-di-tert-butylphenol),
4,4'-methylenebis-(6-tert-butyl-2-methylphenol),
1,1-bis-(5-tert-butyl-4-hydroxy-2-methylphenyl)-butane,
2,6-bis-(3-tert-butyl-5-methyl-2-hydroxybenzyl)-4-methylphenol,
1,1,3-tris-(5-tert-butyl-4-hydroxy-2-methylphenyl)-butane,
1,1-bis-(5-tert-butyl-4-hydroxy-2-methylphenyl)-3-n-dodecylmercaptobutane, ethylene glycol bis-[3,3-bis-(3'-tert-butyl-4'-hydroxyphenyl)-butyrate], bis-(3-tert-butyl-4-hydroxy-5-methylphenyl)-dicyclopentadiene and bis-[2-(3'-tert-butyl-2'-hydroxy-5'-methylbenzyl)-6-tert-butyl-4-methylphenyl] terephthalate.

1.5. Benzyl compounds, for example,
1,3,5-tris-(3,5-di-tert-butyl-4-hydroxybenzyl)-2,4,6-trimethylbenzene,
bis-(3,5-di-tert-butyl-4-hydroxybenzyl) sulfide,
isooctyl-3,5-di-tert-butyl-4-hydroxybenzylmercaptoacetate,
bis-(4-tert-butyl-3-hydroxy-2,6-dimethylbenzyl)-dithiol terephthalate,
1,3,5-tris-(3,5-di-tert-butyl-4-hydroxybenzyl) isocyanurate,
1,3,5-tris-(4-tert-butyl-3-hydroxy-2,6-dimethylbenzyl)isocyanurate, dioctadecyl
3,5-di-tert-butyl-4-hydroxybenzylphosphonate, the Ca salt of monoethyl
3,5-di-tert-butyl-4-hydroxybenzylphosphonate and 1,3,5-tris-(3,5-dicyclohexyl-4-hydroxybenzyl)isocyanurate.

1.6. Acylaminophenols, for example 4-hydroxylauranilide, 4-hydroxystearanilide, 2,4-bis-(octylmercapto)-6-(3,5-di-tert-butyl-4-hydroxyanilino)-s-triazine and octyl N-(3,5-di-tert-butyl-4-hydroxyphenyl)-carbamate.

1.7. Esters of β-(3,5-di-tert-butyl-4-hydroxyphenyl)-propionic acid with monohydric or polyhydric alcohols, for example with methanol, octadecanol, 1,6-hexanediol, neopentyl glycol, thiodiethylene glycol, diethylene glycol, triethylene glycol, pentaerythritol, tris-(hydroxyethyl)isocyanurate and N,N'-bis-(hydroxy)ethyloxamide.

1.8. Esters of β-(5-tert-butyl-4-hydroxy-3-methylphenyl)-propionic acid with monohydric or polyhydric alcohols, for example with methanol, octadecanol, 1,6-hexanediol, neopentyl glycol, thiodiethylene glycol, diethylene glycol, triethylene glycol, pentaerythritol, tris-(hydroxy)ethyl isocyanurate and N,N'-bis-(hydroxyethyl)oxamide.

1.9. Esters of β-(3,5-dicyclohexyl-4-hydroxyphenyl)-propionic acid with monohydric or polyhydric alcohols, for example with methanol, octadecanol, 1,6-hexanediol, neopentyl glycol, thiodiethylene glycol, diethylene glycol, triethylene glycol, pentaerythritol, tris-(hydroxy)ethyl isocyanurate and N,N'-bis-(hydroxyethyl)oxamide.

1.10. Amides of β-(3,5-di-tert-butyl-4-hydroxyphenyl)-propionic acid, for example,
N,N'-bis-(3,5-di-tert-butyl-4-hydroxyphenylpropionyl)-hexamethylenediamine,
N,N'-bis-(3,5-di-tert-butyl-4-hydroxyphenylpropionyl)-trimethylenediamine and
N,N'-bis-(3,5-di-tert-butyl-4-hydroxyphenylpropionyl)-hydrazine.

2. UV absorbers and light stabilizers 2.1. 2-(2'-Hydroxyphenyl)-benzotriazoles, for example the 5'-methyl-,3',5'-di-tert-butyl-, 5'-tert-butyl-,5'(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy-, 3',5'-di-tert-amyl- or 3',5'-bis-(α,α-dimethylbenzyl)- derivative.

2.2. 2-Hydroxybenzophenones, for example the 4-hydroxy-, 4-methoxy-, 4-octoxy-, 4-decyloxy-, 4-dodecyloxy-, 4-benzyloxy-, 4,2',4'-trihydroxy- or 2'-hydroxy-4,4'-dimethoxy-derivative.

2.3. Esters of substituted or unsubstituted benzoic acids, for example 4-tert-butylphenyl salicylate, phenyl salicylate, octylphenyl salicylate, dibenzoylresorcinol, bis-(4-tert-butylbenzoyl)-resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylates, for example ethyl or isooctyl α-cyano-β,β-diphenylacrylate, methyl α-carbomethoxycinnamate, methyl or butyl α-cyano-β-methyl-p-methoxycinnamate, methyl α-carbomethoxy-p-methoxycinnamate and N-(β-carbomethoxy-β-cyanovinyl)-2-methylindoline.

2.5 Nickel compounds, for example nickel complexes of 2,2'-thiobis-[4-(1,1,3,3-tetramethylbutyl)-phenol], such as the 1:1 complex or the 1:2 complex, if appropriate with additional ligands, such as n-butylamine, triethanolamine or N-cyclohexyldiethanolamine, nickel dibutyldithiocarbamate, nickel salts of monoalkyl 4-hydroxy-3,5-di-tert-butylbenzylphosphonates, such as the methyl or ethyl ester, nickel complexes of ketoximes, such as 2-hydroxy-4-methylphenyl undecyl ketoxime, and nickel complexes of 1-phenyl-4-lauroyl-5-hydroxypyrazole, if appropriate with additional ligands.

2.6. Sterically hindered amines, for example bis-(2,2,6,6-tetramethylpiperidyl) sebacate, bis-(1,2,2,6,6-pentamethylpiperidyl) sebacate, bis-(1,2,2,6,6-pentamethylpiperidyl) n-butyl-3,5-di-tert-butyl-4-hydroxybenzylmalonate, the condensation product formed from 1-hydroxyethyl-2,2,6,6-tetramethyl-4-hydroxypiperidine and succinic acid, the condensation product formed from N,N'-bis-(2,2,6,6-tetramethyl-4-piperidyl)-hexamethylenediamine and 4-tert-octylamino-2,6-dichloro-1,3,5-s-triazine, tris-(2,2,6,6-tetramethyl-4-piperidyl) nitrilotriacetate, tetrakis-(2,2,6,6-tetramethyl-4-piperidyl) 1,2,3,4-butanetetraoate and 1,1'-(1,2-ethanediyl)-bis-(3,3,5,5-tetramethylpiperazinone).

2.7. Oxamides, for example 4,4'-di-octyloxyoxanilide, 2,2'-di-octyloxy-5,5'-di-tert-butyloxanilide, 2,2'-di-dodecyloxy-5,5'-di-tert-butyloxanilide, 2-ethoxy-2'-ethyloxanilide, N,N'-bis-(3-dimethylaminopropyl)-oxamide, 2-5-tert-butyl-2'-ethyloxanilide and a mixture thereof with 2-ethoxy-2'-ethyl-5,4'-di-tert-butyloxanilide or mixtures of o-methoxy- and p-methoxy-disubstituted oxanilides and of o-ethoxy- and p-ethoxy-disubstituted oxanilides.

2.8. 2-(2-Hydroxyphenyl)-1,3,5-triazines, for example 2,4,6-tris-(2-hydroxy-4-octyloxyphenyl)-1,3,5-triazine, 2-(2-hydroxy-4-octyloxyphenyl)-4,6-bis-(2,4-dimethylphenyl)-1,3,5-triazine, 2-(2,4-dihydroxyphenyl)-4,6-bis-(2,4-dimethylphenyl)-1,3,5-triazine, 2,4-bis-(2-hydroxy-4-propyloxyphenyl)-6-(2,4-dimethylphenyl)-1,3,5-triazine, 2-(2-hydroxy-4-octyloxyphenyl)-4,6-bis-(4-methylphenyl)-1,3,5-triazine and 2-(2-hydroxy-4-dodecyloxyphenyl)-4,6-bis-(2,4-dimethylphenyl)-1,3,5-triazine.

3. Metal deactivators, for example N,N'-diphenyloxamide, N-salicylal-N'-salicyloylhydrazine, N,N'-bis-(salicyloyl)-hydrazine, N,N'-bis-(3,5-di-tert-butyl-4-hydroxyphenylpropionyl)-hydrazine, 3-salicyloylamino-1,2,4-triazole and bis-(benzylidene)-oxalic acid dihydrazide.

4. Phosphites and phosphonites, for example triphenyl phosphite, diphenyl alkyl phosphites, phenyl dialkyl phosphites, tris-(nonylphenyl) phosphite, trilauryl phosphite, trioctadecyl phosphite, distearyl pentaerythrityl diphosphite, tris-(2,4-di-tert-butylphenyl) phosphite, diisodecyl pentaerythrityl diphosphite, bis-(2,4-di-tert-butylphenyl) pentaerythrityl diphosphite, tristearyl sorbitol triphosphite, tetrakis-(2,4-di-tert-butylphenyl) 4,4'-biphenylenediphosphonite and 3,9-bis-(2,4-di-tert-butylphenoxy)-2,4,8,10-tetraoxa-3,9-diphosphaspiro[5.5]undecane.

5. Compounds which destroy peroxides, for example esters of β-thiodipropionic acid, for example the lauryl, stearyl, myristyl or tridecyl ester, mercaptobenzimidazole, the zinc salt of 2-mercaptobenzimidazole, zinc dibutyldithiocarbamate, dioctadecyl disulfide and pentaerythrityl tetrakis-(β-dodecylmercapto)-propionate.

6. Polyamide stabilizers, for example copper salts in combination with iodides and/or phosphorus compounds and salts of divalent manganese.
7. Basic co-stabilizers, for example melamine, polyvinylpyrrolidone, dicyandiamide, triallyl cyanurate, urea derivatives, hydrazine derivatives, amines, polyamides, polyurethanes, alkali and alkaline earth metal salts of higher fatty acids, for example Ca stearate, Zn stearate, Mg stearate, Na ricinoleate and K palmitate, antimony pyrocatecholate or tin pyrocatecholate.
8. Nucleating agents, for example 4-tert-butylbenzoic acid, adipic acid or diphenylacetic acid.
9. Fillers and reinforcing agents, for example calcium carbonate, silicates, glass fibres, asbestos, talc, kaolin, mica, barium sulfate, metal oxides and hydroxides, carbon black and graphite.
10. Other additives, for example plasticizers, lubricants, emulsifiers, pigments, fluorescent brighteners, fire-retarding agents, antistatic agents and blowing agents.

The incorporation of the compounds of the formula I and, if appropriate, further additives into the organic material is carried out by known methods, for example before or during shaping or by applying the dissolved or dispersed compounds to the organic material, if appropriate with subsequent evaporation of the solvent. The compounds of the formula I can also be added to the materials to be stabilized in the form of a master batch containing these compounds in a concentration of, for example, 2.5 to 25% by weight.

The compounds of the formula I can also be added before or during polymerization or before crosslinking.

The compounds of the formula I can be incorporated into the material to be stabilized in a pure form or encapsulated in waxes, oils or polymers.

The materials stabilized in this way can be used in a very wide variety of forms, for example as films, fibres, tapes, moulding materials or profiles or as binders for paints, adhesives or cements.

The compounds of the formula I are also suitable for use as chain terminators in the anionic solution polymerization of 1,3-dienes.

The compounds of the formula I can be prepared analogously to known processes, for example by catalytic alkylation of 2,4-xylenol with α-olefins.

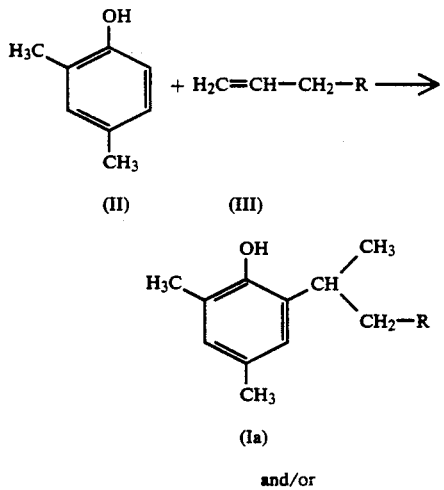

and/or

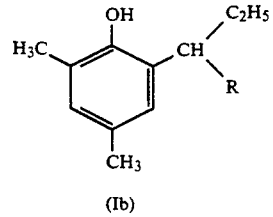

R is alkyl. α-Olefin mixtures wherein R is, for example, $C_{13}-C_{17}$alkyl, $C_{17}-C_{21}$alkyl or $C_{21}-C_{27}$alkyl can also be employed as compounds of the formula (III).

The reaction is appropriately carried out at temperatures of 80°-250° C., preferably 130°-200° C., in the presence of a catalyst. The following may be mentioned as suitable catalysts:

a) inorganic and organic acids, for example sulfuric acid or p-toluenesulfonic acid;
b) zeolites, for example ZSM zeolite;
c) acid earths, for example ®Fulmont 234, ®Fulcat 14 or ®Fulmont 700;
d) Friedel-Crafts catalysts, as described, for example, in Kozlikovski Ya. B. et al., Zh. Org. Khim. 23, 1918-24 (1987); Laan J.A.M.; Chem. Ind. 1, 34-35 (1987) and Kurashev M.V. et al.; Izv. Akad. Nauk. SSSR, Ser. Khim 8, 1843-1846 (1986); and
e) activated γ-aluminium oxide, as described, for example, in DE-B 1,142,873 and U.S. Pat. No. 3,367,981.

Activated γ-aluminium oxide is particularly preferred as the catalyst.

If a mixture of the compounds (Ia) and (Ib) is produced in the preparation of the compounds of the formula I, this mixture can be separated with the aid of for example, chromatographic processes, in particular gas chromatography and high-pressure liquid chromatography (HPLC).

Since the compounds of the formula I can be produced as mixtures in their preparation, the invention also relates to a mixture of the compounds.

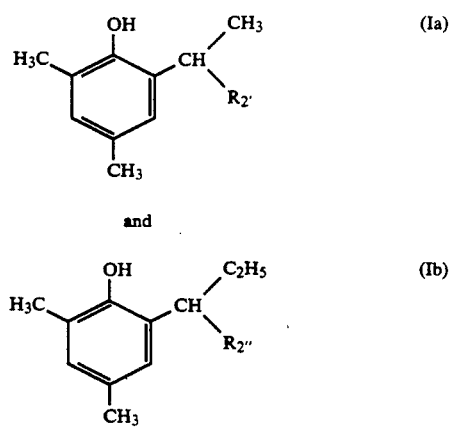

in which $R_2'$ is $-C_mH_{2m+1}$ and $R_2''$ is $-C_{m-1}H_{2m-1}$ and m is an integer from 8 to 30 and is the same in the radicals $R_2'$ and $R_2''$.

A mixture of the compounds

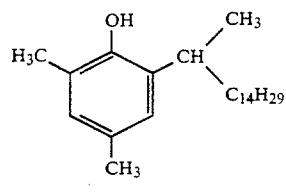

and

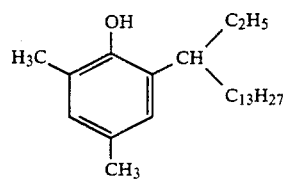

is preferred. A mixture of the compounds

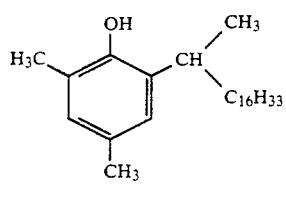

and

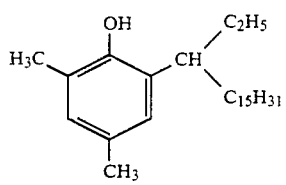

is also preferred. The compounds of the formula I can be obtained by reacting 2,4-xylenol with an $\alpha$-$C_{10}$-$C_{30}$alkene in the presence of a catalyst.

The following examples illustrate the invention further. In these examples, parts and percentages are by weight unless anything to the contrary is stated.

EXAMPLE 1

Preparation of 2,4-dimethyl-6-sec-octadecylphenol 756 g of $\alpha$-octadecene (purity: 85%), 366.5 g of 2,4-xylenol and 30 g of activated $\gamma$-aluminium oxide (treated as described in DE-B-1,142,873, Example 1) as catalyst are charged to an autoclave (2000 ml). The reaction mixture is heated to 310° C. and is stirred for 15 hours at this temperature. After cooling, the catalyst is filtered off. The crude product is distilled at 200°–225° C. and 1 kPa. The product obtained is a colourless wax and is in the form of a mixture of 2,4-dimethyl-6-(1-methylheptadecyl)-phenol and 2,4-dimethyl-6-(2-ethylhexadecyl)phenol in a ratio of 74/11.

If desired, the mixture of isomers can be separated by chromatographic methods (for example gas chromatography or high-pressure liquid chromatography).

Yield: 770 g (=67% of theory).

Melting point: ~30° C.

Elementary analysis: Calculated: C=83.35%; H=12.38%. Found: C=83.49%; H=12.32%.

EXAMPLE 2a

Preparation of 2,4-dimethyl-6-sec-hexadecylphenol

The preparation is carried out analogously to Example 1. 672 g of $\alpha$-hexadecene (purity: 92%) and 366.5 g of 2,4-xylenol are employed as the reactants. The resulting product is a colourless liquid and is in the form of a mixture of 2,4-dimethyl-6-(1-methylpentadecyl)-phenol and 2,4-dimethyl-6-(2-ethyltetradecyl)-phenol in a ratio of 81/7.

If desired, the mixture of isomers can be separated by chromatographic methods.

Yield: 749 g (=72% of theory).

Boiling point: 170°–200° C. at 1 kPa.

EXAMPLE 2b

Preparation of 2,4-dimethyl-6-sec-hexadecylphenol 220 g (1 mol) of linear $\alpha$-hexadecene (purity: 92%), 122 g (1 mol) of 2,4-xylenol and 10 g of activated ZSM-zeolite as catalyst are initially placed in an autoclave holding 0.75 l. The reaction mixture is heated to 220° C. and is stirred for 15 hours at this temperature. After cooling, the catalyst is filtered off and the unreacted starting materials (xylenol: boiling point=40° C. at $10^{-1}$ mbar; $\alpha$-hexadecene: boiling point=60°–70° C. at $8 \times 10^{-2}$ mbar) are removed by distillation. The liquid residue is then distilled under a high vacuum ($10^{-2}$ mbar) at 142°–147° C.

The product is a colourless liquid and is in the form of a mixture of 2,4-dimethyl-6-(1-methylpentadecyl)-phenol and 2,4-dimethyl-6-(2-ethyltetradecyl)-phenol in a ratio of 56/11.

If desired, the mixture of isomers can be separated by chromatographic methods.

Elementary analysis: Calculated: C=83.17%; H=12.21%. Found: C=83.14%; H=12.08%.

EXAMPLE 3a

Preparation of 2,4-dimethyl-6-sec-dodecylphenol

The preparation is carried out analogously to Example 1. The product obtained is in the form of a mixture of 2,4-dimethyl-6-(1-methylundecyl)-phenol and 2,4-dimethyl-6-(1-ethyldecyl)-phenol in a ratio of 53/25.

If desired, the mixture of isomers can be separated by chromatographic methods.

Boiling point: 175° C. under 4 mbar.

EXAMPLE 3b

Preparation of 2,4-dimethyl-6-sec-dodecylphenol

The preparation is carried out analogously to Example 1. The product obtained is in the form of a mixture of 2,4-dimethyl-6-(1-methylundecyl)-phenol and 2,4-dimethyl-6-(1-ethyldecyl)-phenol in a ratio of 73/15.

If desired, the mixture of isomers can be separated by chromatographic methods.

Boiling point: 180° C. under 4 mbar.

EXAMPLE 4

Preparation of a mixture of 2,4-dimethyl-6-sec-($C_{20}$-$C_{24}$alkyl)-phenol

The preparation is carried out analogously to Example 1. 2,4-Xylenol and an $\alpha$-olefin mixture ($H_2C=CH-CH_2-R$ in which R=$C_{17}$-$C_{21}$alkyl) are employed as the reactants. The reaction mixture obtained contains 2,4-dimethyl-6-(1-methylnonadecyl)-phenol, 2,4-dimethyl-6-(1-methylheneicosyl)-phenol and 2,4-dimethyl-6-(1-methyltricosyl)-phenol in a ratio of 45/35/3. The product is in the form of a viscous oil.

If desired, the mixture can be separated by chromatographic methods.

Elementary analysis: Calculated: C=83.88%; H=12.84%. Found: C=84.12%; H=13.22%.

EXAMPLE 5

Preparation of a mixture of 2,4-dimethyl-6-sec-($C_{24}$-$C_{30}$alkyl)-phenol

The preparation is carried out analogously to Example 1. 2,4-Xylenol and an α-olefin mixture ($H_2C=CH-CH_2-R$ in which $R=C_{21}$-$C_{27}$alkyl) are employed as the reactants. The reaction mixture obtained contains 2,4-dimethyl-6-(1-methyltricosyl)-phenol, 2,4-dimethyl-6-(1-methylpentacosyl)-phenol, 2,4-dimethyl-6-(1-methylheptacosyl)-phenol and 2,4-dimethyl-6-(1-methylnonacosyl)-phenol in a ratio of 15/35/33/14. The product is in the form of a wax.

If desired, the mixture can be separated by chromatographic methods.

Boiling point: 50°-60° C.

EXAMPLE 6

Stabilization of acrylonitrile/butadiene/styrene terpolymer (ABS).

The additives indicated in Table 1 or Table 2 are dissolved in 40 ml of a hexane/isopropanol solvent mixture. The solution is added with vigorous stirring to a dispersion of 100 g of ABS in 600 g of water, the solution being completely absorbed by the ABS in a short time (approx. one minute). The ABS powder is filtered off with suction and dried in vacuo for 40 hours at 40° C. 2% of titanium dioxide (pigment) and also 1% of ethylene bis-stearamide (slip agent) are added to the dry powder. The mixture is then compounded for 4 minutes on a twin-roll mill at 180° C.

A sheet 0.8 mm thick is compressed from the milled hide at 175° C., and test specimens measuring 45×17 mm² are punched out. The effectiveness of the additives put in is tested by heat ageing in a circulating air oven at 180° C. The development of colour after 45 minutes testing time serves as a criterion. The colour intensity is determined by the "Yellowness Index" as specified in ASTM D 1925-70. Higher numbers mean a more intense yellow coloration. The tests show that the yellow coloration is effectively suppressed by the addition of the compounds according to the invention.

TABLE 1

| Additive | Yellowness Index after 45 minutes at 180° C. |
|---|---|
| — | 78 |
| 0.5% of DLTDP | 75 |
| 0.25% of the compound from Example 2b + 0.5% of DLTDP | 44 |

DLTDP: dilauryl thiodipropionate

TABLE 2

| Additive | Yellowness Index after 45 minutes at 180° C. |
|---|---|
| — | 58 |
| 0.5% of DLTDP | 66 |
| 0.25% of the mixture from Example 4 + 0.5% of DLTDP | 34 |
| 0.25% of the mixture from | 36 |

TABLE 2-continued

| Additive | Yellowness Index after 45 minutes at 180° C. |
|---|---|
| Example 5 + 0.5% of DLTDP | |

DLTDP: dilauryl thiodipropionate

EXAMPLE 7

Stabilization of Methyl Methacrylate/Butadiene/Styrene Graft Copolymer (MBS).

Preparation of the Additive Emulsion

A mixture of 6.4 parts of the compound described in Example 2a, 25.6 parts of dilauryl thiodipropionate and 3.4 parts of stearic acid is heated to fusion (about 80° C.). The mixture is vigorously stirred and a warm solution of 0.4 parts solid sodium hydroxide and 21.4 parts of water is added. The obtained emulsion (water droplets in organic medium) is then converted by adding 42.8 parts of warm water. Subsequently, the emulsion is diluted 1/10 with warm water and gently stirred at 60° C. until use.

COAGULATION CONDITIONS

The amount of additive emulsion indicated in Table 3 is added to 100 ml of cooled MBS-latex. The mixture is stirred for 30 minutes. Then, the mixture is poured into 200 ml of aqueous HCl (0.1N) at 70° C. The final temperature is about 60° C. Subsequently, the mixture is vigorously stirred and about 20 ml of aqueous NaOH (1N) are added in order to adjust the pH to 5.5-6. The suspension is heated up to 95° C. and this temperature is maintained for 5 minutes.

Finally, the suspension is filtered, the solid MBS is washed with water and dried for 48 hours at 60° C. under vacuum. The diameter of the MBS particles is about 3 to 10 μm.

The MBS-powder is exposed to a thermal analysis at 200° C. in the air. The exothermic reaction which appears is a measure for the degradation of the polymer. The criterion for stabilization is the time to onset ($T_o$) or the time to the maximum ($T_m$) of the exothermic reaction. The results shown in Table 3 reveal a good stabilization of the polymer.

TABLE 3

| Concentration of the additive emulsion in MBS-latex | $T_o$ in minutes | $T_m$ in minutes |
|---|---|---|
| 1%* | 9-11 | 14-16 |

*This value corresponds to 3% in dried MBS

What is claimed is:

1. A composition containing a) a polystyrene, substituted polystyrene, copolymer or terpolymer of styrene or of a substituted styrene, polycarbonate, polyestercarbonate, polyurethane, polyamide, copolyamide, polyacetyl or polyphenylene oxide and b) an effective stabilizing amount of a compound of the formula I

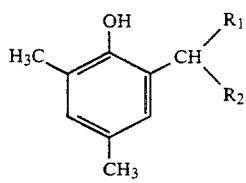

in which R₁ is methyl or ethyl and R₂ is $C_{10}$-$C_{30}$alkyl.

2. A composition according to claim 1, wherein R₂ is $C_{12}$-$C_{18}$alkyl.

3. A composition according to claim 1, wherein the compound of the formula I is

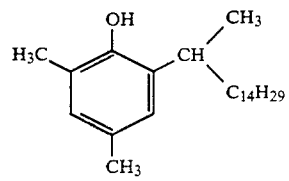

or

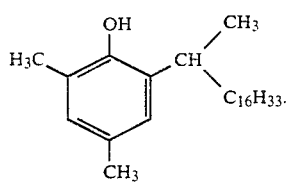

4. A composition according to claim 1, containing a mixture of the compounds

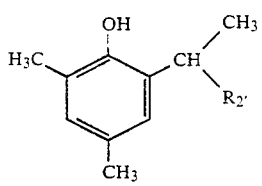

and

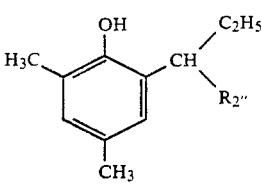

in which $R_2'$ is —$C_mH_{2m+1}$ and $R_2''$ is —$C_{m-1}H_{2m-1}$ and m is an integer from 10 to 30 and is the same in the radicals $R_2'$ and $R_2''$.

5. A composition according to claim 1, wherein the component a) is a polystyrene, substituted polystyrene or a copolymer or terpolymer of styrene or of a substituted styrene.

6. A composition according to claim 1, wherein the component a) is impact-resistant polystyrene, a styrene/acrylonitrile copolymer or an acrylonitrile/butadiene/styrene terpolymer.

7. A composition according to claim 1, wherein the component a) is an acrylonitrile/butadiene/styrene terpolymer or a methyl methacrylate/butadiene/styrene graft copolymer.

8. A composition according to claim 1, wherein the component a) is a polycarbonate, polyester-carbonate, polyurethane, polyamide, copolyamide, polyacetal or polyphenylene oxide.

9. Compounds of the formula I,

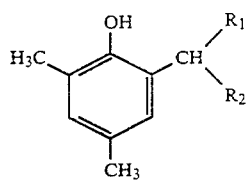

in which R₁ is methyl or ethyl and R₂ is $C_{10}$-$C_{30}$alkyl.

10. A composition containing a) an organic material which is sensitive to thermal, oxidative or actinic degradation and b) an effective stabilizing amount of a compound of the formula I according to claim 9.

11. A mixture of the compounds

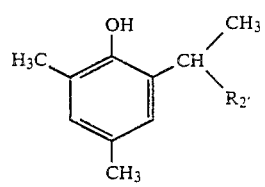

and

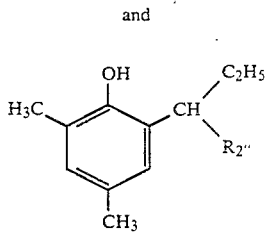

in which $R_2'$ is —$C_mH_{2m+1}$ and $R_2''$ is —$C_{m-1}H_{2m-1}$ and m is an integer from 10 to 30 and is the same in the radicals $R_2'$ and $R_2''$.

12. A mixture of the compounds

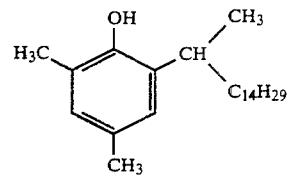

and

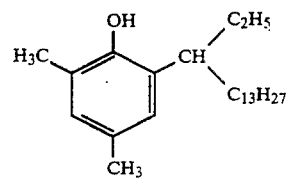

according to claim 11.

13. A mixture of the compounds

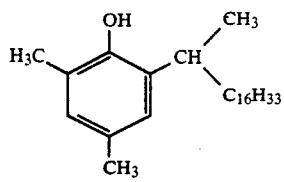

and

-continued

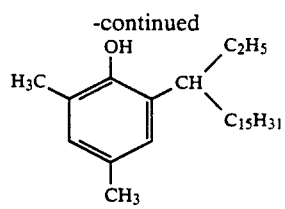

according to claim 11.

14. A process for the stabilization of polystyrene, substituted polystyrene, copolymers or terpolymers of styrene or of a substituted styrene, polycarbonate, polyester-carbonate, polyurethane, polyamide, copolyamide, polyacetal or polyphenylene oxide against thermal, oxidative or actinic degradation, which comprises incorporating an effective stabilizing amount of a compound of the formula I defined in claim 1 into these materials.

* * * * *